(12) United States Patent
Illum et al.

(10) Patent No.: US 6,387,917 B1
(45) Date of Patent: May 14, 2002

(54) SALTS OF OPIOID ANALGESICS, PARTICULARLY MORPHINE, AND METHODS OF USING SAME

(75) Inventors: Lisbeth Illum; Peter Watts, both of Nottingham; Ian Lafferty, Leicestershire; Alan Smith, Nottingham, all of (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 09/692,088

(22) Filed: Oct. 19, 2000

(30) Foreign Application Priority Data

Oct. 20, 1999 (GB) ................................................ 9924797

(51) Int. Cl.⁷ ..................... A61K 31/485; C07D 489/04
(52) U.S. Cl. .......................................... 514/282; 546/44
(58) Field of Search ............................. 514/282; 546/44

(56) References Cited

U.S. PATENT DOCUMENTS

| | | |
|---|---|---|
| 2,665,227 A | 1/1954 | Clough et al. |
| 4,334,071 A | 6/1982 | Kotick et al. |
| 4,626,539 A | 12/1986 | Aungst et al. |
| 5,607,940 A | 3/1997 | Stephen et al. |
| 5,756,483 A | 5/1998 | Merkus |

FOREIGN PATENT DOCUMENTS

| | | |
|---|---|---|
| EP | 0 623 345 A1 | 11/1994 |
| JP | 9-208465 | 8/1997 |
| WO | 82/03768 A1 | 11/1982 |
| WO | 99/15528 A1 | 4/1999 |
| WO | 00/76314 A1 | 12/2000 |
| WO | 00/76477 A1 | 12/2000 |
| WO | 00/76506 A1 | 12/2000 |
| WO | 00/76507 A1 | 12/2000 |

OTHER PUBLICATIONS

D.R. Karsa and R.A. Stephenson (Eds.), Chemical Aspects of Drug Delivery Systems, p. 43, (1996), The Royal Society of Chemistry, Cambridge, UK.

*Primary Examiner*—Charanjit S. Aulakh
(74) *Attorney, Agent, or Firm*—Akin, Gump, Strauss, Hauer & Feld, L.L.P.

(57) ABSTRACT

The methane sulphonate salt of morphine and compositions thereof have medicinal uses, particularly in the treatment of pain. Compositions comprising a methane sulphonate salt of an opioid analgesic also have medicinal uses, adapted for nasal delivery.

12 Claims, No Drawings

SALTS OF OPIOID ANALGESICS, PARTICULARLY MORPHINE, AND METHODS OF USING SAME

BACKGROUND OF THE INVENTION

The present invention relates generally to new salts of opioid analgesics and more particularly to a new salt of morphine, which can be used in the treatment of pain following parenteral or non-parenteral administration.

Morphine is an opioid analgesic that is widely used to relieve severe pain, although it is also used to a lesser extent for its cough suppressant and anti-diarrheal properties. It was first isolated from an opium extract in the early 1800's but is still used as the gold standard with which new drugs with opioid activity are compared. The drug is basic in nature, the pKa of the tertiary amine is 7.93 (*Therapeutic Drugs*, 2d Ed, Dollery (ed.), Churchill Livingstone, Edinburgh (1999)). Salts of morphine, such as the hydrochloride and, more usually, the sulphate, are available commercially. The drug can be administered by injection (intravenous, intramuscular, epidural, intra-articular, intrathecal) or by oral and rectal routes.

More recently, the delivery of morphine via the nasal route in the form of a nasal spray or gel has been described (International Patent Application publication WO-82/03768). This route affords rapid onset of action and convenience to patients and/or the care-giver. Intranasal morphine has been found to be especially useful in the treatment of breakthrough pain and in the treatment of post-surgical pain.

In some clinical situations it is necessary to give high doses of morphine when a patient has become tolerant to the drug. For example, in the treatment of breakthrough pain a dose of 10–20 mg by injection or nasal spray may be effective, but in some patients much larger doses may be required.

This need for higher doses can present problems in the formulation of a delivery system for nasal administration. The limited solubility of the chosen salt form in the volume that can be administered effectively to the nose (150 μl maximum per nostril) can provide a serious limitation. The solubilities of known salts of morphine in water are listed in the *Merck Inclex* 11th ed., Merck and Co (1989), as shown in Table 1 below.

TABLE 1

Solubility of morphine salts in water

| Salt form | Solubility (One gram dissolves in x parts of water) |
| --- | --- |
| Hydrochloride | 17.5 |
| Hydrobromide | 25 |
| Sulphate | 15.5 |
| Nitrate | 1.5 |
| Lactate | 10 |
| Acetate | 2.25 |
| Tartrate | 11 |
| Valerate | 5 |
| Monobasic phosphate | 5 (U.S. Pat. 2,665,227) |

Based on these solubility data, the maximum concentration of morphine hydrochloride or morphine sulphate (the most commonly used salts) as a simple aqueous solution is approximately 60 mg/ml. This would enable nasal dosing of a maximum of around 20 mg morphine as a single dose (based on dosing 0.15 ml of liquid into each nostril).

When developing novel solution formulations of morphine containing high concentrations of morphine, we have found that the salts described in the prior art are unsuitable, because of an inherently low solubility in water and/or instability at low temperatures and/or incompatibility with formulation additives. Such formulation additives include chitosan as an absorption promoter. Instability can be manifested by the formation of a precipitate or crystals of the drug. This phase separation is enhanced at low temperatures, such as found under refrigeration.

Injectable solutions containing high concentrations of morphine have been described in Japanese published patent application (Kokai) JP 09-208465. Benzoate and/or salicylate salts were employed together with the hydrochloride salt of morphine. An injectable solution (2 ml) was formulated containing 200 mg morphine hydrochloride and 200 mg sodium benzoate.

U.S. Pat. No. 5,607,940 and European published patent application EP-A-0 623 345 have described a formulation of morphine for use by electromotive administration comprising morphine citrate salts.

International Patent Application PCT/US82/00546 has described intranasal formulations for opioid drugs. Any pharmaceutically acceptable form of morphine or its phenolic analogues could be used, e.g., the free base or a pharmaceutically acceptable acid addition salt thereof. The listed salts include hydrochloride, sulphate, tartrate, hydrobromide and lactate.

SUMMARY OF THE INVENTION

We have explored the use of alternative salts of opioid analgesics, such as morphine, suitable for the preparation of physically stable aqueous solutions. Surprisingly, we have found the methane sulphonate salt to be a suitable salt. This salt form is commonly termed "mesylate" or "mesilate". According to one aspect of the present invention there is provided a methane sulphonate salt of morphine. There was no suggestion in the above-described prior art to use the methane sulphonate salt of morphine, and no suggestion that the methane sulphonate salt could be used for the improved solubility of any of the listed opioid drugs, and certainly no suggestion that the methane sulphonate salt of morphine could be advantageous.

The methane sulphonate salts of morphine and other opioid analgesics can provide physically stable aqueous solutions of the drug for parenteral or non-parenteral administration. By parenteral, we mean injection via intravenous, intramuscular, sub-cutaneous, intrathecal, epidural, intra-arterial or intra-articular routes. By non-parenteral, we mean administration either via mucosal surfaces in the nose, lung, buccal cavity, gastrointestinal tract (including the rectum), vagina, or eye or via the dermal layer of the skin ("transdermal"). For transdermal administration, the solution could be especially useful when employing electlically-enhanced delivery (iontophoresis) or ultrasound (sonophoresis).

According to a further aspect of the present invention, there is provided a composition adapted for nasal delivery comprising a methane sulphonate salt of an opioid analgesic, especially morphine. The nasally deliverable composition may form a gel once applied to the nose.

Preferred compositions for nasal delivery are solutions, particularly aqueous solutions, and more particularly aqueous solutions in which the methane sulphonate salt of the opioid analgesic is combined with chitosan or a salt or derivative thereof (hereinafter referred to collectively as "a chitosan compound") to provide an increased absorption of the drug.

The present invention also provides a nasal drug delivery device, which contains as a drug a methane sulphonate salt of an opioid analgesic.

DETAILED DESCRIPTION OF THE INVENTION

The methane sulphonate salt can be prepared by mixing the opioid in base form with an equivalent of methane sulphonic acid and then recovering the product. When morphine base is used, the salt is recovered as a fine white odorless powder or as fine white odorless crystals.

Alternatively and preferably, the salt can be formed in situ by neutralising the opioid with methane sulphonic acid and then using the solution so prepared for medicinal use.

Methane sulphonic acid ($CH_4O_3S$) can be sourced commercially.

While the examples described below are directed to morphine salts, it will be understood by one of ordinary skill in the art based on the present disclosure, that salts of other opioid analgesic drugs could be similarly prepared. By opioid analgesic drugs we include, inter alia, diamorphine, fentanyl, tramadol, hydromorphone, hydrocodeine, codeine, oxycodone, oxymorphone, buprenorphine, meperidine, pentazocine.

Generally, an aqueous pharmaceutical composition, e.g., for nasal administration, can be prepared as follows:

The selected amount of opioid in base form is mixed with an equimolar amount of methane sulphonic acid solution of appropriate molarity (for example 2M). By base form, we mean the drug in the non-salt form. If a chitosan compound is to be added to promote transmucosal absorption from the nasal cavity, then an appropriate amount, as a powder or an aqueous solution, is added to make the final concentration of the chitosan compound in the range of about 5–10 mg/ml. The formulation is adjusted to the desired pH (generally in the range about pH 4–7) by adding additional methane sulphonic acid solution or an alkali (for example sodium hydroxide solution), as appropriate.

By the term "chitosan" we include all derivatives of chitin, or poly-N-acetyl-D-glucosamine, including all polyglucosamines and oligomers of glucosamine materials of different molecular weights, in which the greater proportion of the N-acetyl groups have been removed through hydrolysis (deacetylation). Preferably, the chitosan is produced from chitin by deacetylation to a degree of greater than 40%, preferably about 50% to 98%, and more preferably about 70% to 90%.

Chitosan derivatives or salts of chitosan (e.g., nitrate, phosphate, sulphate, hydrochloride, glutamate, lactate or acetate salts) may also be used instead of chitosan.

We use the term "chitosan derivatives" to include ester, ether or other derivatives formed by bonding of acyl and/or alkyl groups with OH groups, but not the $NH_2$ groups, of chitosan. Examples are O-alkyl ethers of chitosan and O-acyl esters of chitosan. Modified chitosans, particularly those conjugated to polyethylene glycol, are included in this definition.

Low and medium viscosity chitosans (for example, CL113, G210 and CL110) may be obtained from various sources, including Pronova Biopolymer, Drammen, Norway; Seigagaku America Inc., MD, USA; Meron (India) Pvt, Ltd., India; Vanson Ltd, VA, USA; and AMS Biotechnology Ltd., UK. Suitable derivatives include those which are disclosed in Roberts, *Chitin Chemistry*, MacMillan Press Ltd., London (1992).

The chitosan, chitosan derivative or salt used preferably has a molecular weight of about 4,000 Daltons or more, preferably in the range of about 25,000 to about 2,000,000 Daltons, and most preferably in the range of about 50,000 to about 300,000 Daltons. Chitosans of different low molecular weights can be prepared by enzymatic degradation of chitosan using chitosanase or by the addition of nitrous acid. Both procedures are known to those skilled in the art. Preferably, the chitosan compound is water-soluble.

Particularly preferred chitosan compounds, which may be mentioned, include the "Sea Cure®" series of chitosan glutamates available from Pronova Biopolymer, Drammen, Norway.

The opioid analgesic content of the liquid composition will depend upon the potency of the opioid compound. Typically, the amount of opioid analgesic (expressed as base) will be in the range of about 0.5 mg/ml to about 1000 mg/ml, preferably in the range of about 1 mg/ml to about 500 mg/ml.

A morphine methane sulphonate liquid formulation will typically have a morphine content (as base) of about 0.1 mg/ml to about 600 mg/ml, preferably about 10 mg/ml to about 500 mg/mi, and most preferably about 30 mg/ml to about 450 mg/ml.

The liquid formulation can also contain other ingredients such as buffer systems, pH modifiers, anti-oxidants, stabilizing agents, anti-microbial agents, chelating agents, viscosity-enhancing agents, or other agents generally used in pharmaceutical formulations.

The methane sulphonate salt of the opioid analgesic may also be formulated as a powder for intranasal administration. The methane sulphonate salt may be prepared, isolated in powder form, and administered per se, or it may be mixed with other ingredients which include, but are not restricted to, lactose, and starch (to improve powder flow properties) and chitosan (to enhance drug absorption). The methane sulphonate salt may also be administered intranasally as a powder in the form of a microsphere.

The methane sulphonate salt of the opioid analgesic may also be incorporated into a solid dosage form, such as a tablet or capsule, for oral, buccal, rectal or vaginal administration. The tablet or capsule can be formulated to provide immediate release of the drug or to provide sustained release over a prolonged period (typically 6–24 hours). Ingredients which may be incorporated into an immediate release tablet or capsule include, but are not restricted to, lactose, microcrystalline cellulose, sucrose, mannitol, or dicalcium phosphate (as diluents); povidone, polyethylene glycol or starch (as binders); cross-linked carboxymethylcellulose, starch or cross-linked povidone (as disintegrants); and magnesium stearate (a lubricant). Additional ingredients which may also be incorporated into sustained-release tablet or capsule formulations include, but are not restricted to, hydrophilic polymers, such as hydroxypropyl methylcellulose; waxy materials, such as hydrogenated vegetable oil or glyceryl palmitostearate; and synthetic rate-controlling polymers, such as ethylcellulose or methacrylate copolymers. Such solid dosage forms will contain a therapeutically effective dose of the opioid, which for morphine will be equivalent to about 5 mg to about 300 mg of morphine methane sulphonate salt.

Alternatively, a solid dosage form for rectal or vaginal administration may also be prepared by mixing the methane sulphonate salt of the opioid analgesic in powder form with melted fatty base and molding into a suitable shape. Suitable bases include, but are not limited to, cocoa butter, Suppocire® (Gattefosse, France) and Witepsol® (Hüls, Germany).

For delivery across the skin, preferably by a technique such as electrically-assisted transport (iontophoresis), the methane sulphonate salt of the opioid analgesic may be formulated as an aqueous solution or as a water-based gel and then filled into an iontophoretic device. Such devices are applied to the skin and deliver drug into the systemic circulation at a rate which may be constant or varied with time.

The present invention is now illustrated, but not limited, with reference to the following examples.

EXAMPLE 1

Preparation of a Solution Containing 400 mg/ml of Morphine Base (anhydrous), as the Methane Sulphonate Salt A 2 M solution of methane sulphonic acid was prepared by weighing 9.61 g of methane sulphonic acid (Pfaltz & Bauer, Waterbury, Conn., USA) into a 50 ml volumetric flask, dissolving in 40 ml of water, and then making up to volume with water. 8.5 g of morphine base (monohydrate, BPC 1934) (MacFarlan Smith, Edinburgh, UK) was weighed into a 50 ml beaker. An equimolar amount (14.0 ml) of the 2 M methane sulphonic acid solution was stirred into the morphine powder (the molecular weight of morphine base (monohydrate) and methane sulphonic acid are 303 and 96, respectively). An almost clear solution was formed. The solution was transferred to a 20 ml volumetric flask and adjusted to volume by adding water to form a solution containing 400 mg/ml morphine base (anhydrous), as the methane sulphonate salt.

EXAMPLE 2

Preparation of a Solution for Intranasal Administration Containing 150 mg/ml Morphine Base, as the Methane Sulphonate Salt and 5 mg/ml Chitosan Glutamate 1 g of chitosan glutamate (Protasan UPG213, Pronova Biopolymer, Drammen, Norway) was weighed into a 100 ml volumetric flask. 70 ml of water was added and the flask contents stirred until the chitosan had dissolved. The flask contents were made up to 100 ml with water.

8 g of morphine base (monohydrate) (MacFarlan Smith, Edinburgh, UK) was weighed into a 100 ml beaker. An equimolar amount (13.2 ml) of 2 M methane sulphonic acid solution (see Example 1) was stirred into the morphine powder, followed by 25 ml of the chitosan solution. The pH of the solution was measured and adjusted to pH 4 by the addition of 2 M methane sulphonic acid solution. It was then transferred to a 50 ml volumetric flask and made up to volume by addition of water.

A portion of the solution was drawn into a 10 ml syringe and passed through a 0.2 m syringe filter (Sartorius, Leicester, UK). 0.12 ml of this solution was filled into a unit dose, nasal liquid, spray device (Pfeiffer, Radolphzell, Germany). When actuated, the device delivers 0.1 *ml of solution, containing* 15 mg of morphine base (as the methane sulphonate salt).

EXAMPLE 3

Comparative Stability of Morphine Hydrochloride and Morphine Methane Sulphonate Solutions A solution formulation was prepared containing 40 mg/ml morphine hydrochloride (equivalent to 30 mg/ml morphine base) and 5 mg/ml chitosan glutamate, as follows: 100 mg of chitosan glutamate (Protasan UPG213, Pronova Biopolymer, Drammen, Norway) was weighed into a beaker and dissolved by stirring with 15 ml of water. 800 mg of morphine hydrochloride (trihydrate) (MacFarlan Smith) and 74 mg of sodium chloride (Sigma) were added to the chitosan solution and stirred until dissolved. The solution was adjusted to pH 4 using 0.5M hydrochloric acid solution (Fisher, Loughborough, UK), transferred to a 20 ml volumetric flask, and made up to volume with water.

0.14 ml aliquots of this solution were filled into Pfieffer unit dose spray devices. When stored in a refrigerator (2–8° C.) and at room temperature (approx. 18° C.), the morphine in the devices was found to precipitate, although it could be returned to solution by gentle warming. Storage at an elevated temperature (>20° C.) was necessary in order for the morphine to remain in solution.

In contrast, the formulation prepared in Example 2, which contains five fold higher morphine loading (equivalent of 150 mg/ml morphine base) has been shown to remain in solution for in excess of 12 weeks when stored at 2–8° C.

EXAMPLE 4

Oral tablet containing 10 mg morphine base (anhydrous), as the methane sulphonate salt 10 g of micro-crystalline cellulose (MCC) ("Avicel PH102", FMC, Philadelphia, Pa., USA) was weighed into the bowl of a mortar. To the MCC was added 1.7 ml of the solution containing 400 mg/ml morphine (base) as methane sulphonate salt (Example 1). The mortar contents were mixed thoroughly with a pestle and passed through a 1 mm sieve. The sieved material was dried in an oven at 40° C. for 1 hour. The resulting granules were screened through a 0.25 mm sieve. 5 g of dried, sieved granules, 4.9 g of spray-dried lactose ("Zeparox", Borculo, Chester, UK) and 0.1 g of magnesium stearate (BDH, Poole, UK) were weighed into a glass bottle and mixed using a Turbula shaker-mixer (Willy Bachofen, Switzerland). A Manesty F3 tablet press was fitted with round, bi-concave, 7 mm diameter tablet tooling. The machine was used to press tablets from the powder blend in the weight range 300–320 mg. A tablet weighing 310 mg would contain 10 mg morphine base, as the methane sulphonate salt.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A composition adapted for nasal delivery, comprising a methane sulphonate salt of an opioid analgesic.

2. The composition according to claim 1, further comprising chitosan or a salt or derivative thereof.

3. The composition according to claim 1, which comprises a powder, a microsphere, a gel or a gelling solution.

4. A composition according to claim 1, comprising a methane sulphonate salt of morphine.

5. A composition according to claim 4, which is an aqueous solution.

6. A composition according to claim 1, comprising a methane sulphonate salt of morphine and chitosan or a salt or a derivative thereof.

7. A method for treating pain, comprising administering an effective amount of the composition according to claim 4 to the nose of a patient suffering from pain.

8. A method of treating pain, comprising administering to the nose of a patient suffering from pain an effective amount of a methane sulphonate salt of an opioid analgesic.

9. A method of treating pain, comprising administering to the nose of a patient suffering from pain an effective amount of the methane sulphonate salt of morphine.

10. A method of preparation of a solution formulation of morphine adapted for nasal administration, the method comprising neutralizing a suspension of morphine base in water with methane sulphonic acid.

11. A pharmaceutical composition adapted for nasal administration comprising the methane sulphonate salt of morphine.

12. A nasal drug delivery device, containing as a drug a methane sulphonate salt of an opioid analgesic.

* * * * *